(12) United States Patent
Lenardo et al.

(10) Patent No.: US 6,312,648 B1
(45) Date of Patent: Nov. 6, 2001

(54) APPLICATOR SYSTEM

(75) Inventors: Michael J. Lenardo, Potomac, MD (US); Galen Fisher, Princeton, NJ (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/005,475

(22) Filed: Jan. 12, 1998

(51) Int. Cl.[7] ........................................... B01L 3/02

(52) U.S. Cl. ................................ 422/100; 422/102

(58) Field of Search ........................... 422/101, 102, 422/100, 103; 600/573; 215/248, 249, 250; 220/254, 256–259, 265, 266

(56) References Cited

U.S. PATENT DOCUMENTS

| | | | |
|---|---|---|---|
| 2,165,860 | * | 7/1939 | Killmeyer . |
| 2,814,420 | * | 11/1957 | Elder, Jr. et al. . |
| 3,215,500 | | 11/1965 | Bittner . |
| 3,326,401 | | 6/1967 | Long . |
| 3,391,466 | | 7/1968 | Brouwer et al. . |
| 3,512,940 | | 5/1970 | Shapiro . |

(List continued on next page.)

FOREIGN PATENT DOCUMENTS

| | | |
|---|---|---|
| 394 945 | 6/1965 | (CH) . |
| 32 01 691 A1 | 9/1983 | (DE) . |
| 36 28 930 | 5/1988 | (DE) . |
| 995930 | 6/1969 | (EP) . |
| 0 337 677 | 10/1989 | (EP) . |
| 0 341 372 | 11/1989 | (EP) . |
| 0 343 596 A3 | 11/1989 | (EP) . |
| 0 343 596 B1 | 11/1989 | (EP) . |
| 0 392 864 A1 | 10/1990 | (EP) . |
| 0 487 490 A2 | 5/1992 | (EP) . |
| 2 284 842 | 4/1976 | (FR) . |
| 2 373 461 | 7/1978 | (FR) . |
| 63-98380 | 4/1988 | (JP) . |
| WO 95/27180 | 10/1995 | (WO) . |
| WO 96/30274 | 10/1996 | (WO) . |
| WO 98/14276 | 4/1998 | (WO) . |

OTHER PUBLICATIONS

"Choosing the Correct Molecular Weight Cut–Off for Concentration and Desalting: A Guide to Ultrafilter Selection", Amicon A Grace Company: 1–4 (1994).

"Flow Rates of Centriprep, Centricon, Microcon and Centrifree Centrifugal Devices", Amicon A Grace Company: 1–2 (1994).

"Micropure Particle Separators: For samples of up to 350 $\mu$l", Amicon A Grace Company,: 1–6 (1994).

"Passivation of Micron Microconcentrators for Improved Recovery", Amicon A Grace Company, Publication 335: 2 pgs. (Undated).

"Protein and Peptide Recovery from Polyacrylamide Gel with Micropure Inserts and Micron Microconcentrators", Amicon A Grace Company, Publication 311: 2 pgs. (Undated).

"The Fisher Catalog", *Fisher Scientific*, 5 pgs. (1994).

"High–Recovery Micron Microconcentrators: For up to 100x concentration of 50–500 $\mu$l with highest recovery", Amicon A Grace Company: 1–8 (1993).

Amicon Price List, Amicon, Inc. 2 pgs. (1994).

Marusyk R. et al., "A Simple Method for Dialysis of Small–Volume Samples", *Analytical Biochemistry*, 105: 403–404 (1980).

Roder, H. et al. "Kunststoffe in der Verpackung", *Kunststoffe*, 71: 287–293 (1981).

Primary Examiner—Jeffrey Snay
(74) Attorney, Agent, or Firm—Merchant & Gould P.C.

(57) ABSTRACT

The present invention relates to an applicator system including an applicator, an applicator tube, an applicator tube system, and a cap system.

19 Claims, 7 Drawing Sheets

U.S. PATENT DOCUMENTS

| | | |
|---|---|---|
| 4,024,857 * | 5/1977 | Blecher et al. .......................... 128/2 |
| 4,057,168 | 11/1977 | Bosshold . |
| 4,132,225 * | 1/1979 | Whattam ................................. 128/2 |
| 4,215,700 * | 8/1980 | Crouther et al. ..................... 128/763 |
| 4,241,188 | 12/1980 | Materia et al. . |
| 4,250,893 * | 2/1981 | White .................................. 128/765 |
| 4,271,973 | 6/1981 | Quagliaro et al. . |
| 4,289,248 | 9/1981 | Lynn . |
| 4,292,972 | 10/1981 | Pawelchak et al. . |
| 4,456,137 | 6/1984 | Lyman . |
| 4,502,616 * | 3/1985 | Meierhoefer ......................... 222/215 |
| 4,576,185 * | 3/1986 | Proud et al. ......................... 128/760 |
| 4,599,314 * | 7/1986 | Shami .................................. 435/287 |
| 4,674,640 | 6/1987 | Asa et al. . |
| 4,755,356 | 7/1988 | Robbins et al. . |
| 4,763,804 | 8/1988 | O'Connell . |
| 4,872,872 | 10/1989 | Polak . |
| 4,891,134 | 1/1990 | Vcelka . |
| 4,915,847 | 4/1990 | Dillon et al. . |
| 4,921,137 * | 5/1990 | Heijenga ............................... 222/107 |
| 4,956,103 | 9/1990 | Jessop et al. . |
| 4,962,044 | 10/1990 | Knesel, Jr. et al. . |
| 4,990,253 | 2/1991 | Vcelka . |
| 5,047,347 | 9/1991 | Cline . |
| 5,052,588 * | 10/1991 | Schlosser ............................... 222/80 |
| 5,079,170 | 1/1992 | Rosman et al. . |
| 5,084,246 * | 1/1992 | Lyman et al. ........................ 422/101 |
| 5,163,583 | 11/1992 | Whitworth . |
| 5,224,515 | 7/1993 | Foster et al. . |
| 5,225,165 | 7/1993 | Perlman . |
| 5,254,314 | 10/1993 | Yu et al. . |
| 5,270,011 | 12/1993 | Altherr . |
| 5,334,130 | 8/1994 | Glater et al. . |
| 5,376,273 | 12/1994 | Pacheco et al. . |
| 5,380,435 | 1/1995 | Stokes et al. . |
| 5,382,408 | 1/1995 | Perlman . |
| 5,391,496 | 2/1995 | Kayal et al. . |
| 5,398,837 | 3/1995 | Degrassi . |
| 5,407,087 | 4/1995 | Giblin et al. . |
| 5,523,236 | 6/1996 | Nuzzo . |
| 5,916,526 * | 6/1999 | Robbins ............................... 422/102 |

* cited by examiner

APPLICATOR SYSTEM

BACKGROUND OF THE INVENTION

Various containers and apparatus are used for containing and dispensing liquids in laboratory settings. Useful laboratory liquid containers include tubes such as centrifuge tubes and microcentrifuge tubes. Microcentrifuge tubes come in various volumes from about 0.1 mL to about 2.5 mL and are among the most versatile laboratory liquid sample containers. Microcentrifuge tubes often include a cap connected to the tube and conveniently fit various racks and blocks that, for example, place the tubes in arrays compatible with heaters, pipettors, and culture plates. Due to this convenience, microcentrifuge tubes are used in many laboratory operations, such as shaking, heating, centrifuging, and the like, that require that the tube be capped to prevent spilling or evaporation of fluid in the tube. This requires capping and uncapping of the tube before and after each of these operations. Capping and uncapping takes time and provides an opportunity for spilling or contaminating the contents of the tube.

Liquids are most often added to and dispensed from tubes, such as microcentrifuge tubes, using a pipette or pipettor. Pipetting requires that the tube be uncapped and the pipette or pipettor be inserted into the opened tube. Inserting a pipette, a pipettor or other liquid handling device into the tube is inconvenient in several respects. First, the tube must be repeatedly capped and uncapped for each operation with the pipette or pipettor. This repeated capping and uncapping slows procedures using the tube, increases the likelihood of spilling or otherwise contaminating the fluid in the tube, and is generally inconvenient. Second, insertion of a foreign object such as a pipette or pipettor into a sample in the tube allows contamination of the sample by a dirty pipette or pipettor. Such contamination can waste a valuable sample, give erroneous results, or require an expenditure of additional time and materials to prepare a duplicate sample.

What is needed is a liquid handling tube, such as a microcentrifuge tube, that provides for dispensing its fluid contents without uncapping the tube and without inserting a liquid handling device into the tube.

SUMMARY OF THE INVENTION

The present invention relates to an apparatus and method for dispensing fluid from a tube. The invention includes an applicator system including an applicator and an applicator tube. The applicator tube includes a tube, such as a microcentrifuge tube, and a cap including a spout. The spout, which can be sealed, is suitable for dispensing fluid from the capped tube, for example, into a well of an electrophoresis gel. The liquid can be dispensed in a quantifiable manner. Preferably, the spout is a tube having a lumen and a spout end. Removing the spout end allows fluid to flow through the spout. The cap can be molded from the same piece of material as the tube. Alternatively, one or more caps with spouts can be coupled to form a cap system. Preferably, caps in a cap system are configured for engaging tubes in a convenient array, such as the spacing of wells of a 96-well plate or the spacing of channels of a multichannel pipettor. Similarly, one or more applicator tubes can be coupled to form a tube system.

The applicator of the invention is adapted and configured to retain and dispense liquid from a plurality of applicator tubes. Preferably, the applicator includes a handle and a headpiece. The headpiece retains applicator tubes and includes a tube compressor that compresses the tubes for dispensing liquid from the applicator tube. Preferably, the headpiece also includes a tube ejector for removing tubes from the applicator after dispensing.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENT

The Applicator System

Figure 1:
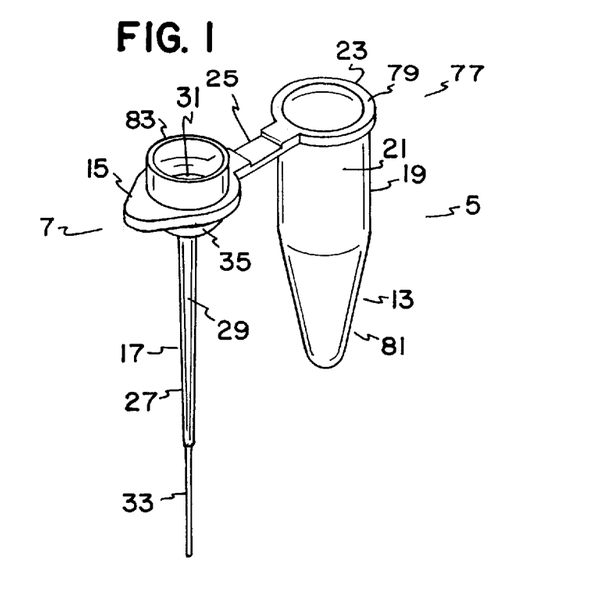
FIG. 1 illustrates a perspective view of an embodiment of an applicator tube of the invention with the tube uncapped.
Figure 2:
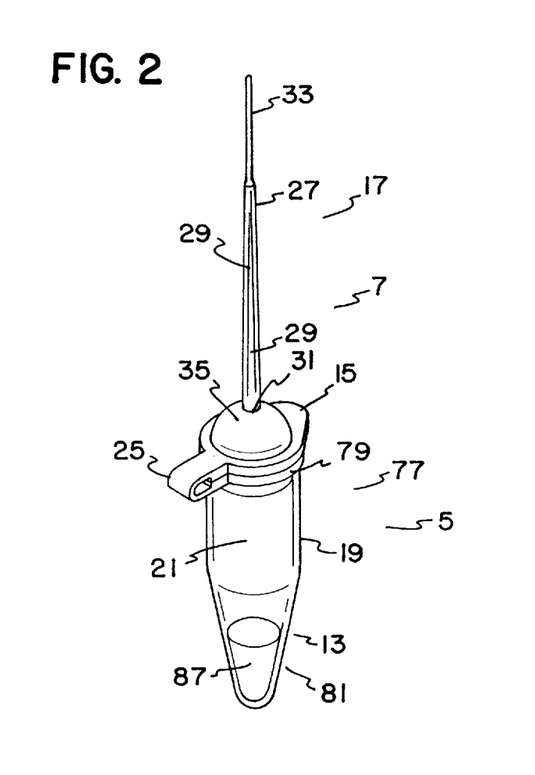
FIG. 2 illustrates a perspective view of the embodiment of the applicator shown in FIG. 2 with the cap snappably engaging the tube.
Figure 3:
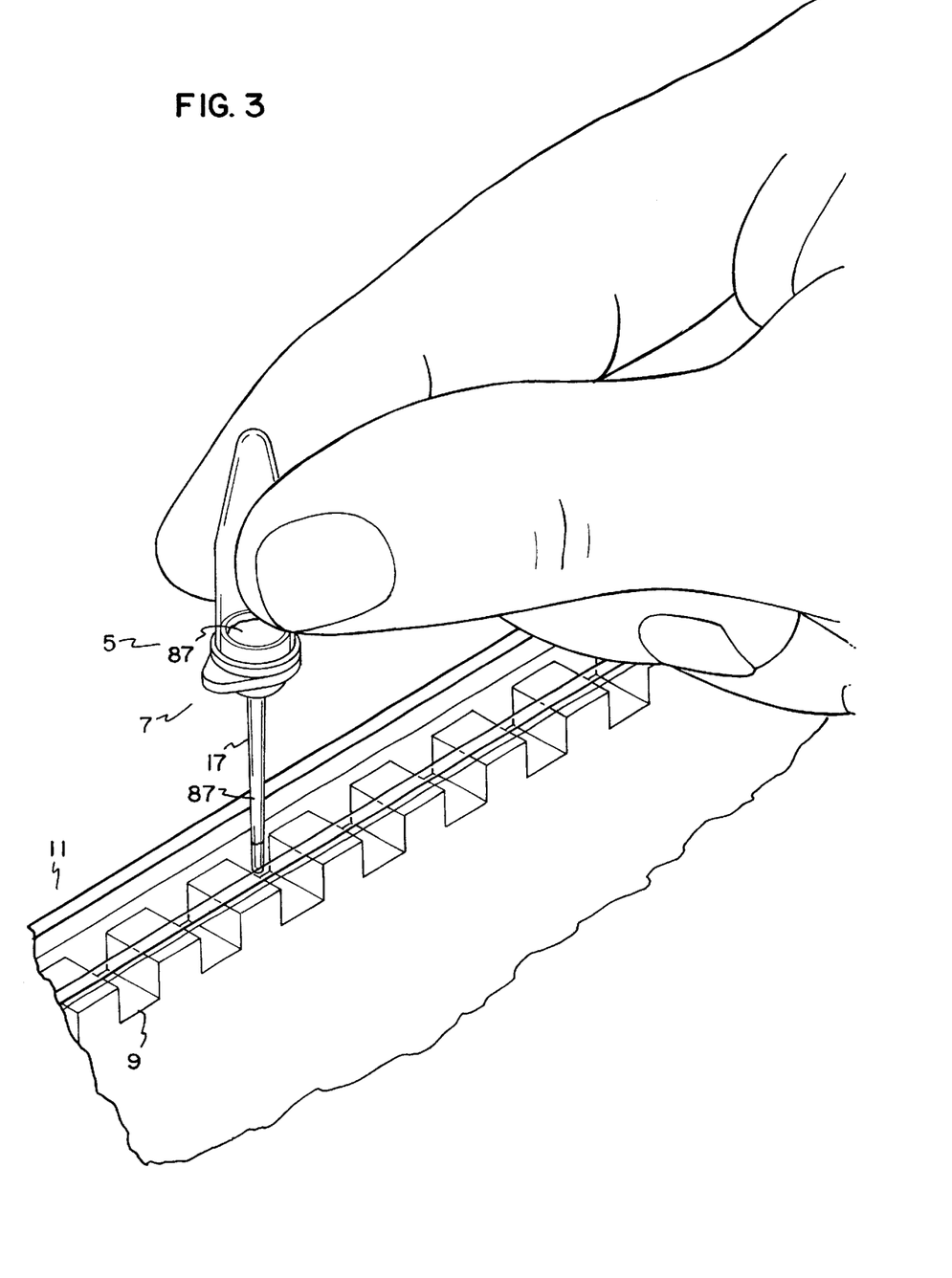
FIG. 3 illustrates a perspective view of manual dispensing of fluid from an applicator tube into a well of an electrophoresis gel.
Figure 8:
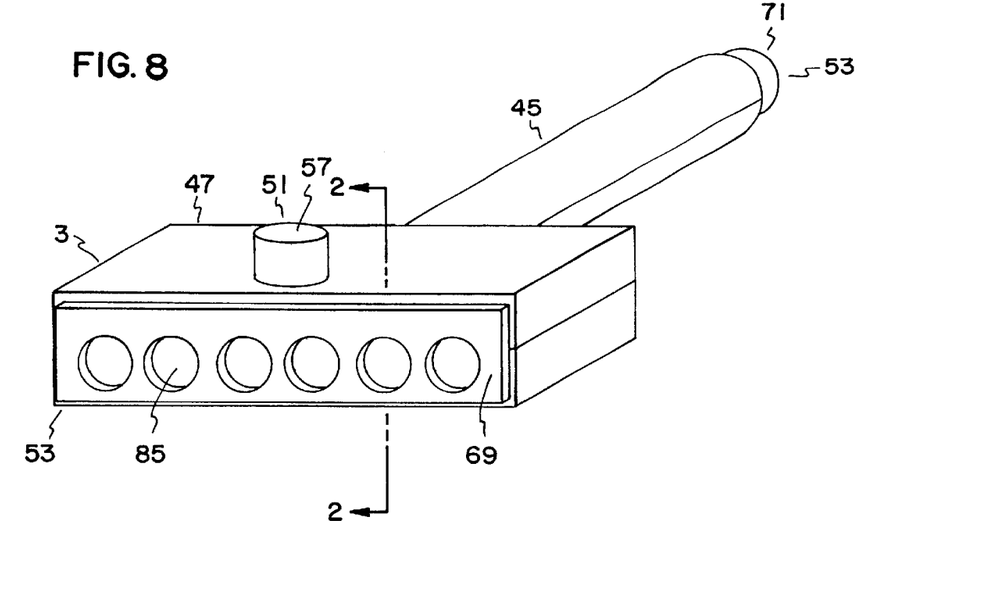
FIG. 8 illustrates an embodiment of an applicator system of the invention showing a front right a perspective view of the applicator.
Figure 9:
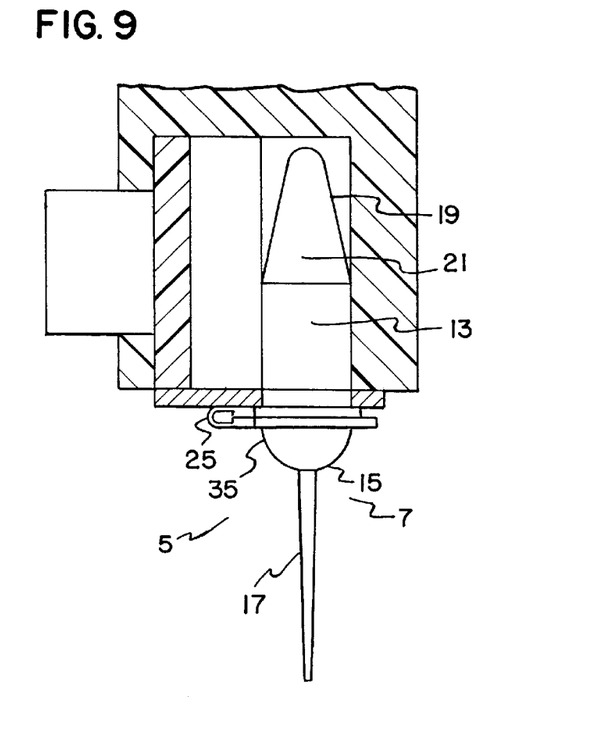
FIG. 9 shows a cross-sectional view of a fragment of the applicator system illustrating an applicator tube in the applicator.

The present invention relates to a system for dispensing a fluid or liquid sample 87 from a tube suitable for containing liquid sample 87 during heating. As shown in FIGS. 8 and 9, applicator system 1 includes an applicator 3 and an applicator tube 5. Applicator tube 5 includes applicator cap 7 (FIGS. 1 and 2). Applicator system 1 can dispense liquid 87 from applicator tube 5 into receptacles such as a well 9 of an electrophoresis gel 11 (FIG. 3).

The Applicator Tube and Cap

In reference to FIGS. 1 and 2, applicator tube 5 includes a tube 13 and an applicator cap 7, which includes a cap 15 and a spout 17. Tube 13 includes a tube body 19 defining both a tube cavity 21 and an open end 23. Cavity 21 is adapted and configured to hold fluid 87. Applicator tube 5 can be any of a variety of types of tubes from which fluids can be dispensed through a spout. Advantageously, tube 13 is deformable so that tube 15 can be squeezed or compressed (FIGS. 3 and 8–11) for dispensing liquid through spout 17. Applicator tube 5 is, preferably, made of a material such, as polypropylene, that withstands repeated compression and also freezing and thawing, so that a single sample can be stored for later use and also dispensed multiple times in aliquots from a single tube. Due to spout 17, repeated dispensing can be accomplished without capping and uncapping of and without insertion of a pipet or pipettor into applicator tube 5.

Typically, tube 13 has a volume of about 0.05 mL to about 15 mL, preferably about 0.1 mL to about 1.5 mL, preferably about 0.1 mL to about 0.4 mL. As shown in FIGS. 1 and 2, tube 13 typically has a shape including a combination of a generally cylindrical rim portion 77 and a generally conical portion 81. In other embodiments, tube 13 can have a generally cylindrical shape or a generally conical shape. Tube 13 is preferably adapted and configured for use in a microcentrifuge and in laboratory heating blocks. Tube 13 is preferably a tube suitable for containing reactions of the polymerase chain reaction.

Figure 4:
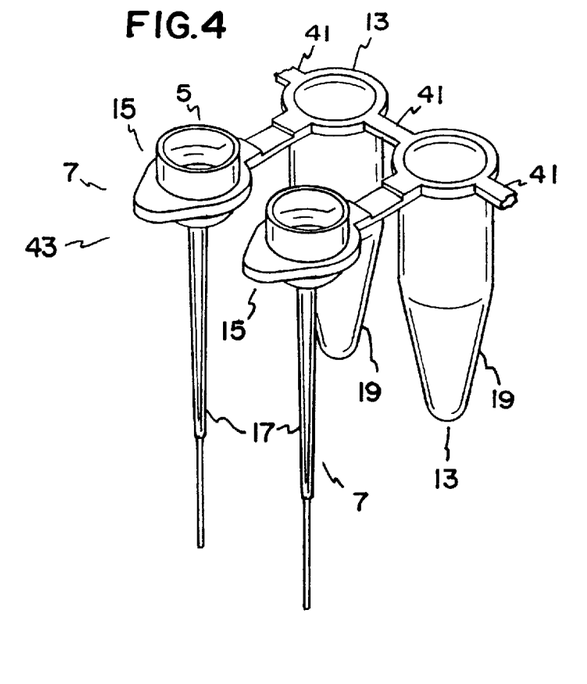
FIG. 4 illustrates a perspective view of an embodiment of an applicator tube system of the invention.

Applicator tube 5 can be provided in several different embodiments. For example, in FIGS. 1 and 2, applicator tube 5 is a single molded component including tube 13, cap 15, and spout 17. In another embodiment, illustrated in FIG. 4, applicator tube 5 is part of a tube system 43 including a plurality of applicator tubes 5. In tube system 43, each applicator tube is connected to one or more other applicator tubes 5 by a tube tab 41. Tube system 43 preferably includes six, eight, or twelve applicator tubes 5 connected, preferably, with the spacing of wells of a 96-well plate (about 0.3–0.4 in. between centers of adjacent tube openings 23), with the spacing suitable for dispensing with a multichannel pipettor (about 0.3–0.5 in. between centers of adjacent tube openings 23), or with spacing suitable for other racks, equipment, or dispensers. Advantageously, tube system 43 keeps a plurality of applicator tubes 5 in a predetermined order, to reduce the chance that samples are used out of the predetermined order in subsequent testing.

Figure 6:
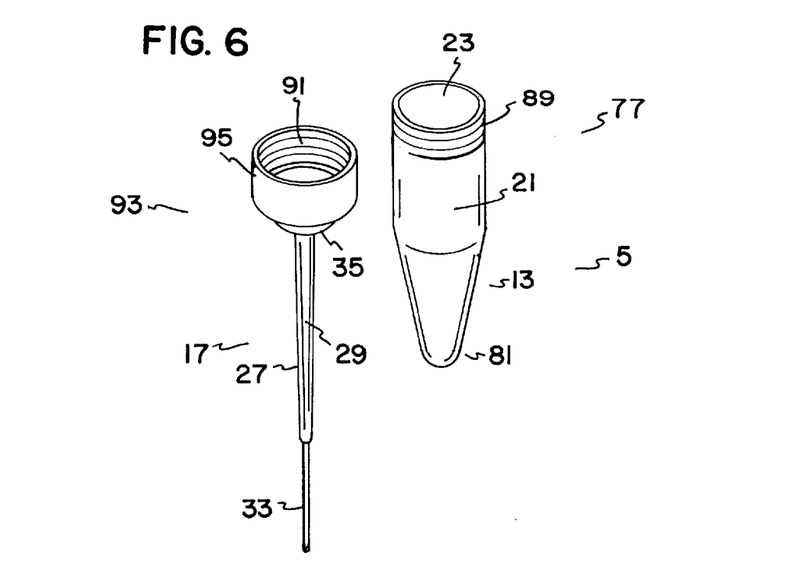
FIG. 6 illustrates a perspective view of an embodiment of an applicator tube of the invention with the tube uncapped and including a threaded applicator cap and a threaded tube.
Figure 7:
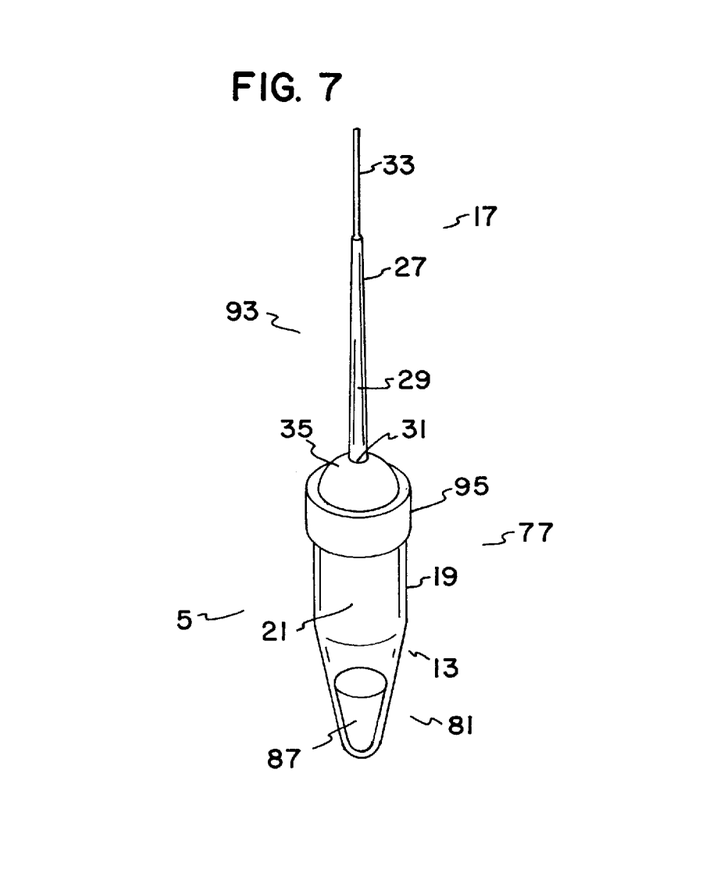
FIG. 7 illustrates a perspective view of the embodiment of the applicator shown in FIG. 6 with the cap threadably engaging the tube.

Tube 13 also includes features for convenient handling and for engaging cap 15 (FIGS. 1 and 2). Configurations for coupling tubes, such as microcentrifuge tubes, and their caps are known to those of skill in the art. Caps can snappably engage open end 23 of tube 13, for example, by snappably engaging a portion of cap 15 with generally cylindrical rim portion 77 of tube 13. Such caps and tubes are shown in FIGS. 1 and 2. Advantageously, rim portion 77 provides strength to open end 23 and provides a convenient surface for gripping or retaining tube 13, preferably, employing flange 79. As shown in FIGS. 6 and 7, rim portion 77 of tube 13 can have tube threads 89 adapted and configured to threadably engage threaded applicator cap 93.

Cap 15 is attached, or coupled, to spout 17 and is adapted and configured to engage tube 13 and to close off open end 23 of tube body 19. Cap 15 includes a lid portion 35. Lid portion 35 is dome shaped as illustrated in FIG. 1, but can be generally disk shaped. Lid portion 35 defines a cap aperture 31 which is in fluid (liquid-flow) communication with spout 17. Advantageously, cap aperture 31 is centrally located in lid portion 35. Cap 15 is attached to tube 13 by a cap retainer 25. Cap 15, or applicator cap 7, and tube 13 are molded from a single piece of plastic in a preferred embodiment. Cap 15 is preferably configured to snappably engage tube 13 by cap snap portion 83, which fits into tube rim portion 77. In an alternative embodiment, threaded applicator cap 93 includes cap threads 91 in cylindrical cap body 95. Threaded applicator cap 93 is adapted and configured to threadably engage tube threads 89 of tube 13.

Spout 17 includes a spout body 27 and defines a spout lumen 29 (FIGS. 1 and 2). Typically, spout 17 is generally tubular in shape, and the generally tubular shape defines a generally cylindrical spout lumen 29. Tubular spout 17 can be tapered, as shown in FIGS. 1 and 2, to provide lumen 29 with a diameter at an end distal from cap 15 that is smaller than its diameter proximal to cap 15. Spout lumen 29 is sealed by spout end 33, and is opened to the surroundings by removing spout end 33, such as by cutting, breaking, or snapping off spout end 33. When spout end 33 is removed, spout lumen 29 and cap aperture 31 are adapted and configured to provide fluid communication between tube cavity 21 and the surroundings. For example, when cap 15 is engaged with and closes off the end of tube body 19, liquid 87 in tube cavity 21 can be dispensed through spout lumen 29 into the surroundings of the tube, such as into well 9 of electrophoresis gel 11 (FIG. 3). As shown in FIGS. 1 and 2, cap 15 and spout 17 are formed from a single piece of molded plastic. Alternatively, cap 15 and spout 17 can be separate pieces of plastic that are coupled or sealed to form a unit suitable for dispensing liquids.

Figure 5:
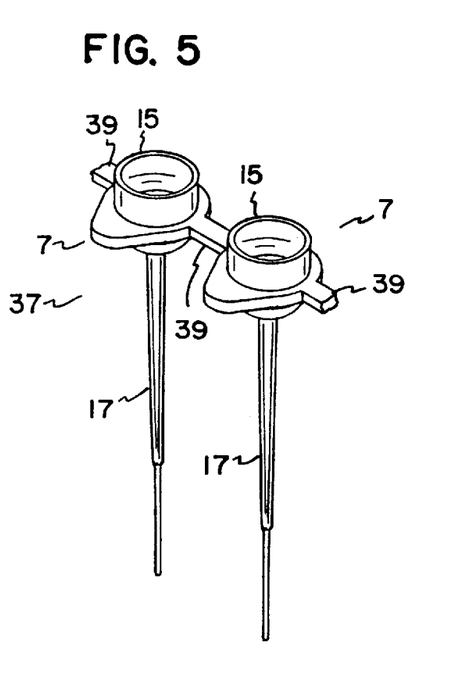
FIG. 5 illustrates a perspective view of an embodiment of a cap system of the invention.

Applicator cap 7 can be provided in several different embodiments. For example, in FIGS. 1 and 2, applicator cap 7 is part of applicator tube 5, such as by being coupled to tube 13. In another embodiment, applicator cap 7 is provided individually as a single unit. In yet another embodiment, illustrated in FIG. 5, applicator cap 7 is a component of a cap system 37, which includes a plurality of applicator caps 7, each connected to one or more other applicator caps 7 by a cap tab 39. Cap system 37 preferably includes six, eight, or twelve applicator caps 7 connected, preferably, with the spacing of wells of a 96-well plate (about 0.3–0.4 in. center to center), with the spacing suitable for dispensing from tubes using multichannel pipettor (about 0.3–0.5 in. center to center), or with spacing suitable for other racks, equipment, or dispensers.

Applicator tube 5 and applicator cap 7 can be made of materials and by methods suitable for other liquid handling tubes, as known in the art. For example, plastic, particularly polypropylene, is a suitable material for making tubes and caps of the invention. Typically, liquid handling tubes are formed by molding plastic, and such molding is suitable for making tubes and caps of the invention.

Applicator tube 5 and cap 7 of the invention are advantageous compared to structures of the prior art. The present applicator tube 5 or cap 7 dispenses liquid 87 though spout 17 without removing cap 15 from tube 13 and without inserting a pipettor or other liquid handling device into tube 13. Use of spout 17 thus prevents spilling of the contents of tube 13 during handling for capping and uncapping and prevents contamination of the contents by a pipettor or other liquid handling device.

Methods of Dispensing

The invention also relates to a method of dispensing a fluid 87 from an applicator tube 5 of the invention. This method includes adding fluid 87 to the cavity 21 defined by tube 13. Fluid 87 is retained in cavity 21 by cap 15 which is engaged on open end 23 of tube 13 to close off open end 23 of tube 13. When it is desired to dispense fluid 87, applicator tube 5 is oriented so that fluid 87 to be dispensed is adjacent to cap aperture 31. Compressing tube 13 results in fluid 87 being dispensed. Fluid 87 that has been added to tube 13 is first brought into contact with cap 15 and cap aperture 31. Compressing tube 13 then urges fluid 87 through lumen 29 of spout 17 and into the surroundings of applicator tube 5, such as into well 9 of electrophoresis gel 11.

The method can include additional steps as well. For example, the closed tube containing fluid can be heated and/or centrifuged. For applicator tubes including a closed spout end 33, the method includes removing spout end 33 before compressing tube 13. The method can also include sealing spout 17, for example by heat sealing, to reform spout end 33, which is advantageous for storage. Alternatively, opened spout 17 can be plugged or covered to seal applicator tube 5 for storage.

The Applicator

FIGS. 8–13 illustrate embodiments of applicator 3 which dispenses fluid from applicator tube 5. Applicator 3 includes a handle 45 and a headpiece 47. Headpiece 47 is adapted and configured to dispense fluid from applicator tube 5, preferably by compressing applicator tube 5. Handle 45 is adapted and configured for manipulation of headpiece 47 and applicator 3. For example, handle 45 can be employed to position applicator 3 and one or more applicator tubes 5 in or over wells 9 of electrophoresis gel 11.

Figure 10:
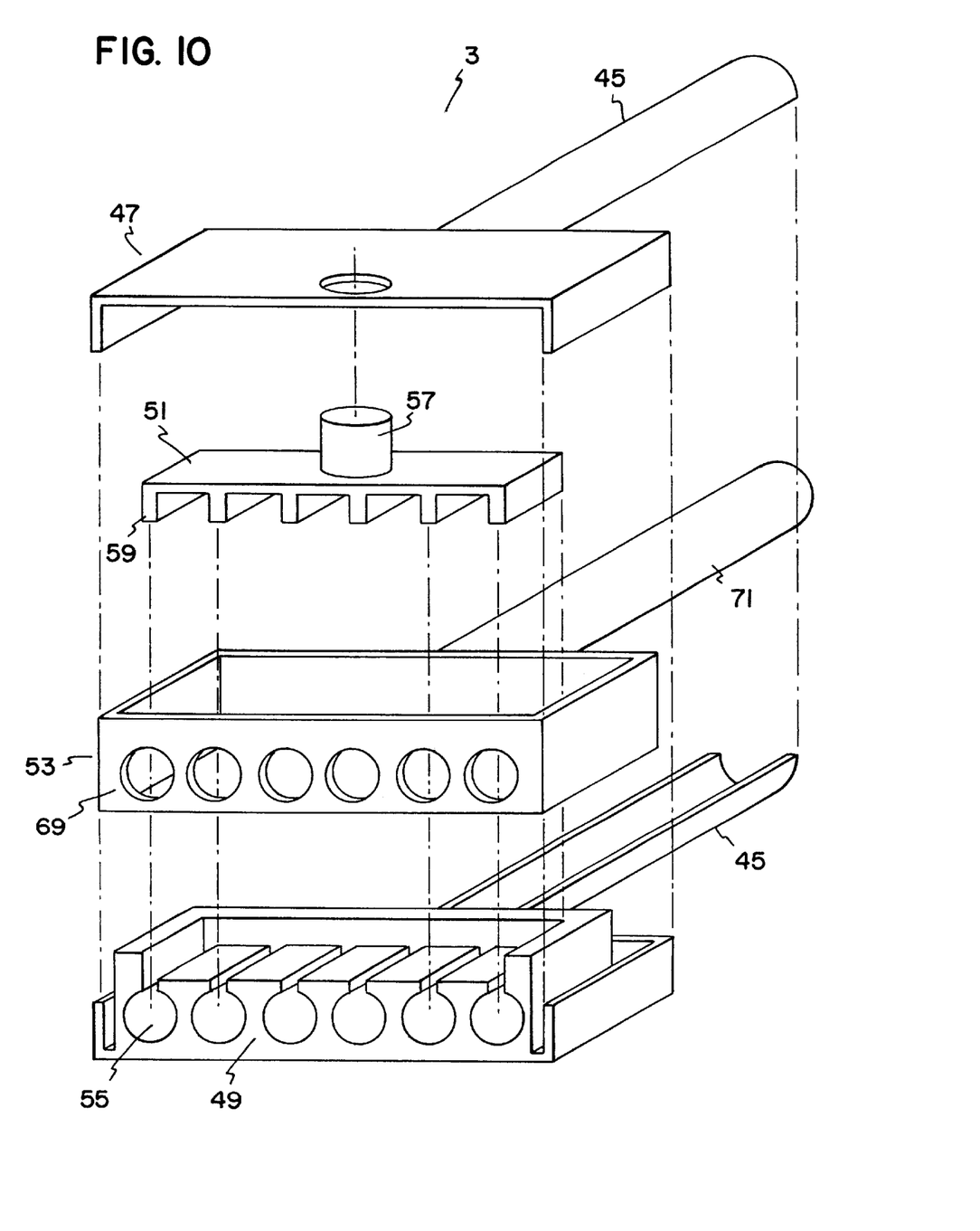
FIG. 10 illustrates an exploded, perspective view of an embodiment an applicator.

In FIGS. 8–10, headpiece 47 includes a tube retaining block 49, a tube compressor 51, and a tube ejector 53. Tube retaining block 49 is adapted and configured for housing and retaining an applicator tube, for example, by friction in a block cavity 55 defined by retaining block 49 and sized closely to diameter of tube 15. Cavity 55 preferably has a shape corresponding to the shape of tube 15. For example, generally cylindrical cavity 55, shown in FIG. 10, can house a generally cylindrical or generally conical tube 15. Alternatively, in another embodiment, a generally conical cavity 55 can house a generally conical tube 15, and the like.

Tube compressor 51 is adapted and configured for compressing one or more tubes 15 retained in block 49. Tube compressor 51 functions to receive an external force and to transmit that force to compress tube 15. For example, in an embodiment shown in FIGS. 8–10, pressing force transfer member 57 transmits force to one or more tube engaging members 59 which contact and compress tube 15. For example, while grasping handle 45, an operator presses force transfer member 57 with a thumb, which compresses applicator tube 5. Preferably, before compressing applicator tube 5, applicator 3 is oriented to bring fluid in applicator tube 5 into contact with cap aperture 23. Compressing applicator tube 5 then results in liquid contents of applicator tube 5 in being urged out into the surroundings through spout 17. In a typical use, one or more applicator tubes 5 are suspended by applicator 3 above one or more wells 9 of electrophoresis gel 11.

When it is desired to remove applicator tube 5 from applicator 3, for example, after liquid had been dispensed from applicator tube 5, tube ejector 53 (shown in FIGS. 8–10) can be actuated to push or eject one or more applicator tubes 5 from applicator 3. Tube ejector 53 is adapted and configured for ejecting one or more applicator tubes 5 from tube retaining block 49. In one embodiment, tube ejector 53 includes a tube ejector member 69 and an ejector actuator member 71. Pressing ejector actuator member 71 pushes applicator tube 5 from applicator 3. For example, an operator presses ejector actuator member 71, which transmits force through tube ejector member 69 to applicator tube 5. Typically, ejector aperture 85 contacts applicator tube 5 at rim portion 77, for example at tube flange 79, and urges tube 13 out of cavity 55. This can be done over a suitable waste container. Alternatively, applicator tube 5 can be recovered for storage and/or further dispensing of its fluid contents.

Figure 11:
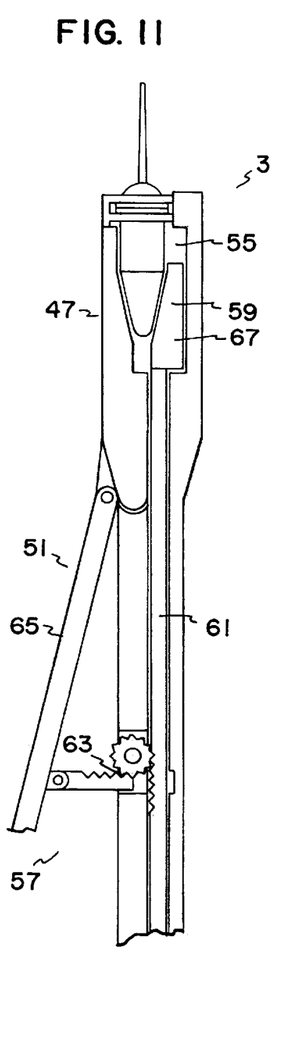
FIG. 11 illustrates a side plan view of an embodiment of an applicator system.
Figure 12:
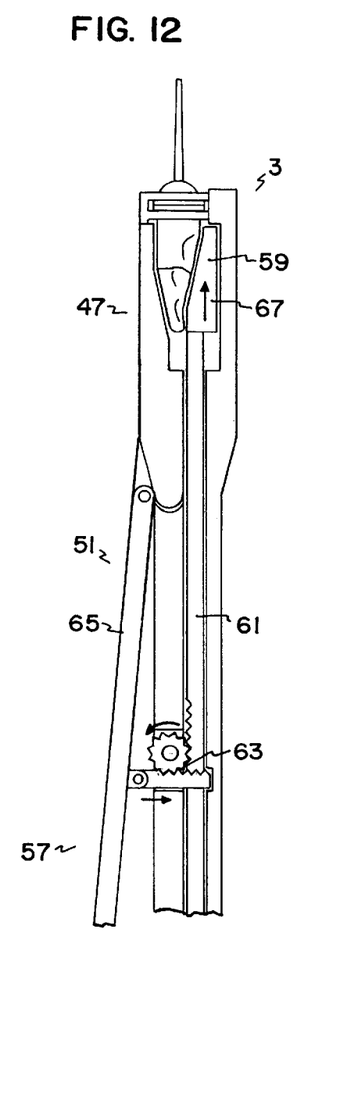
FIG. 12 illustrates a side plan view of an embodiment of an applicator system after compressing the compression handle and compressing the applicator tube with the wedge shaped engaging member.
Figure 13:
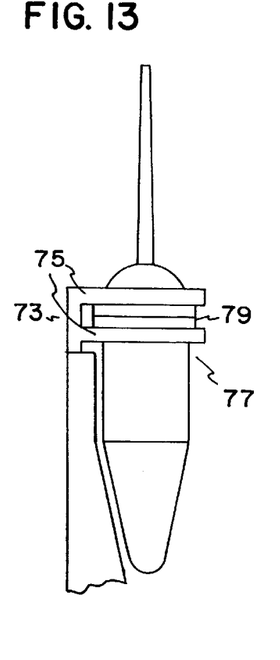
FIG. 13 illustrates an enlarged fragment side plan view of an embodiment of an applicator system showing the tines of the tube retention fork.

In an embodiment illustrated in FIGS. 11–13, applicator 3 is adapted and configured for compressive deformation of tube 13 for dispensing fluid. Compressive deformation of tube 13 is accomplished by an embodiment of tube compressor 51 that includes a wedge shaped tube engaging member 67, and force transfer member 57 includes a push rod 61, a coupling gear 63 (for example a rack and pinion), and a compression handle 65. Wedge shaped tube engaging members 67 are positioned adjacent to or protruding into block cavity 55 and are coupled to push rod 61. Push rod 61, gear 63, and compression handle 65 are coupled to transfer force, upon actuation, or pressing of, compression handle 65, to wedge shaped engaging members 67. Wedge shaped engaging members 67 compress applicator tube 5 and dispense liquid from applicator tube 5. Compressing handle 65 turns coupling gear 63, which advances push rod 61 and wedge shaped engaging member 67 toward and against tube 13. Advancing wedge shaped engaging member 67 compresses and deforms tube 17 and urges fluid from applicator tube 5 through spout 17, as described above.

Advantageously, in the embodiment shown in FIGS. 11–13, applicator tube 17 is retained in applicator 3 for compressive deformation. In the embodiment illustrated, applicator tube 5 is retained in applicator 3 by tube retention fork 73. Tube retention fork 73 includes a pair of tines 75, which engage tube flange 79 of rim portion 77 of tube 13. For inserting and removing or ejecting tubes from applicator 3, tube retention fork 73 moves away from cavity 55, for example by swiveling, to remove tines 75 from flange 79 and to release tube 13.

The various embodiments described above are provided by way of illustration only and should not be construed to limit the invention. Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art upon review of the present specification. The claims are intended to cover such modifications and devices.

What is claimed is:

1. An applicator tube for dispensing fluid into an opening of a well of an electrophoresis gel, the applicator tube comprising:

a microcentrifuge tube including a deformable tube body defining a tube cavity and an open end, the cavity being adapted and configured to hold fluids;

a cap defining a cap aperture, the cap being adapted and configured to engage the tube body and to close off the open end of the tube body; and a spout including a spout body and defining a spout lumen; the spout being coupled to the cap; the spout lumen and cap aperture being adapted and configured for fluid communication with the tube cavity when the cap is engaged with the tube body for closing off the open end of the tube body; the spout lumen being adapted and configured for dispensing fluid from the tube body;

wherein the spout body comprises a tube defining the spout lumen and the tube is closed at an end distal from the cap by an integral spout end attached to the spout body at a junction between the spout end and spout body, a diameter of the spout end adjacent to the junction being smaller than a diameter of the spout body adjacent to the junction; the integral spout end being adapted and configured to be snapped off, cut off, or broken off of the spout body at a point distal to the junction; thereby opening the tube end for dispensing fluid from the tube body; and wherein, for a spout end having a diameter adjacent to the junction smaller than the opening of a well of an electrophoresis gel, breaking, snapping or cutting the spout end will result in a portion of the spout body that is able to be placed inside the opening of a well of an electrophoresis gel to dispense the fluid.

2. The applicator tube of claim 1, wherein the tube is tapered so that the lumen has a smaller diameter at a tube end distal to the cap than at a tube end proximal to the cap.

3. The applicator tube of claim 1, wherein the cap comprises a dome shaped lid portion that defines the cap aperture.

4. The applicator tube of claim 3, wherein the cap aperture is centrally located on the lid portion.

5. The applicator tube of claim 1, wherein the microcentrifuge tube and the cap comprise a single piece of molded plastic.

6. The applicator tube of claim 5, wherein the microcentrifuge tube, the cap, and the spout comprise the single piece of molded plastic.

7. A tube system comprising:

a plurality of applicator tubes for dispensing fluid into an opening of a well of an electrophoresis gel, each applicator tube comprising:

a microcentrifuge tube including a tube body defining a tube cavity and an open end, the cavity being adapted and configured to hold fluids;

a cap defining a cap aperture, the cap being adapted and configured to engage the tube body and to close off the open end of the tube body; and a spout including a spout body and defining a spout lumen; the spout being coupled to the cap; the spout lumen and cap aperture being adapted and configured for fluid communication with the tube cavity when the cap is engaged with the tube body for closing off the open end of the tube body, the spout lumen being adapted and configured for dispensing fluid from the tube body;

wherein the spout body comprises a tube defining the spout lumen and the tube is closed at an end distal from the cap by an integral spout end attached to the spout body at a junction between the spout end and spout body, a diameter of the spout end adjacent to the junction being smaller than a diameter of the spout body adjacent to the junction; the integral spout end being adapted and configured to be snapped off, cut off, or broken off of the spout body at a point distal to the junction; thereby opening the tube end for dispensing fluid from the tube body; and wherein, for a spout end having a diameter adjacent to the junction smaller than the opening of a well of an electrophoresis gel, breaking, snapping or cutting the spout end will result in a portion of the spout body that is able to be placed inside the opening of a well of an electrophoresis gel to dispense the fluid;

one applicator tube being connected to one or more other applicator tubes by the cap of one applicator tube being connected to the cap of one or more other applicator tubes by a cap tab.

8. The tube system of claim 7, wherein the applicator tubes are connected with spacing of wells in a 96-well plate.

9. The tube system of claim 7, comprising 6 or 8 connected applicator tubes.

10. The tube system of claim 7, wherein the applicator tubes are connected with spacing for dispensing with a multichannel pipettor.

11. A cap for a microcentrifuge tube for dispensing fluid into an opening of a well of an electrophoresis gel, the cap comprising:

a cap member defining a cap aperture, the cap member being adapted and configured to engage a microcentrifuge tube and to close off an open end of the microcentrifuge tube;

a spout including a spout body and defining a spout lumen; the spout being coupled to the cap member; the spout lumen and cap aperture being adapted and configured for fluid communication with an interior of the microcentrifuge tube when the cap is engaged with the microcentrifuge tube closing off the open end of the microcentrifuge tube, the spout lumen being adapted and configured for dispensing fluid from the microcentrifuge tube;

wherein the spout body comprises a tube defining the spout lumen and the tube is closed at an end distal from the cap by an integral spout end attached to the spout body at a junction between the spout end and spout body, a diameter of the spout end adjacent to the junction being smaller than a diameter of the spout body adjacent to the junction; the integral spout end being adapted and configured to be snapped off, cut off, or broken off of the spout body at a point distal to the junction; thereby opening the tube end for dispensing fluid from the tube body; and wherein, for a spout end having a diameter adjacent to the junction smaller than the opening of a well of an electrophoresis gel, breaking, snapping or cutting the spout end will result in a portion of the spout body that is able to be placed inside the opening of a well of an electrophoresis gel to dispense the fluid.

12. The cap of claim 11, wherein the tube defining the spout lumen is tapered so that the lumen has a smaller diameter at a tube end distal to the cap than at a tube end proximal to the cap.

13. The cap of claim 11, wherein the cap member comprises a dome shaped lid portion that defines the cap aperture, the cap aperture being centrally located on the lid portion.

14. The cap of claim 11, wherein the cap comprises an engagement member adapted and configured to engage the microcentrifuge tube.

15. The cap of claim 14, wherein the engagement member comprises a flange portion and a generally cylindrical engaging portion.

16. The applicator tube of claim 11, wherein a single piece of molded plastic includes the cap and the spout.

17. A cap system comprising:

a plurality of caps, each cap according to claim 11;

one said cap being connected to one or more other said caps by a cap tab.

18. The cap system of claim 17, wherein the caps are adapted and configured for engaging tubes in a format of a 96-well plate.

19. The cap system of claim 17, wherein the caps are adapted and configured for engaging tubes arranged for dispensing with a multichannel pipettor.

* * * * *